United States Patent
Sardo et al.

(10) Patent No.: US 11,559,061 B2
(45) Date of Patent: Jan. 24, 2023

(54) METHOD AND ASSEMBLY FOR THE TREATMENT OF THE ATMOSPHERE IN A STORAGE SPACE FOR VEGETABLE PRODUCTS

(71) Applicant: XEDA INTERNATIONAL S.A., Saint Andiol (FR)

(72) Inventors: Alberto Sardo, Chateaurenard (FR); Stefano Sardo, Chateaurenard (FR)

(73) Assignee: XEDA INTERNATIONAL S.A., Saint Andiol (FR)

( * ) Notice: Subject to any disclaimer, the term of this patent is extended or adjusted under 35 U.S.C. 154(b) by 136 days.

(21) Appl. No.: 16/312,270

(22) PCT Filed: Jun. 20, 2017

(86) PCT No.: PCT/EP2017/065102
§ 371 (c)(1),
(2) Date: Dec. 20, 2018

(87) PCT Pub. No.: WO2017/220587
PCT Pub. Date: Dec. 28, 2017

(65) Prior Publication Data
US 2019/0159470 A1 May 30, 2019

(30) Foreign Application Priority Data

Jun. 20, 2016 (FR) ..................... 16 55717
Aug. 30, 2016 (FR) ..................... 16 58046

(51) Int. Cl.
*A23B 7/144* (2006.01)
*A23L 3/3409* (2006.01)
(Continued)

(52) U.S. Cl.
CPC ............ *A23B 7/144* (2013.01); *A23L 3/3409* (2013.01); *A61L 9/145* (2013.01); *B01D 1/00* (2013.01);
(Continued)

(58) Field of Classification Search
CPC . A23L 3/3409; B01D 53/1493; B01D 53/346; B01D 53/72; B01D 53/62;
(Continued)

(56) References Cited

U.S. PATENT DOCUMENTS 5,451,248 A 9/1995 Sadkowski et al.
7,638,114 B1 12/2009 Schur
(Continued)

FOREIGN PATENT DOCUMENTS

CN 102596365 A 7/2012
CN 205106215 U 3/2016
(Continued)

OTHER PUBLICATIONS

Search Report of corresponding PCT Application No. PCT/EP2017/065102—2 pages (dated Sep. 4, 2017).
(Continued)

*Primary Examiner* — Subbalakshmi Prakash
(74) *Attorney, Agent, or Firm* — Knobbe, Martens, Olson & Bear, LLP

(57) ABSTRACT

A method of treating the atmosphere of a storage of vegetable products with a volume greater than 200 m$^3$, wherein the method comprises at least one step of contacting the atmosphere with a liquid flow by circulation in a packing. A treatment unit of the atmosphere of a storage of vegetable products having a volume greater than 200 m$^3$, wherein the unit comprises a contacting device comprising a packing, a device for injecting a liquid flow into the contacting device, a device for circulating the storage atmosphere in the
(Continued)

contacting device, wherein the contacting device is so designed that the atmosphere is brought into contact with the liquid flow by circulation in the packing.

12 Claims, 5 Drawing Sheets

(51) Int. Cl.

| | | |
|---|---|---|
| *A61L 9/14* | (2006.01) | |
| *B01D 53/14* | (2006.01) | |
| *B01D 53/34* | (2006.01) | |
| *B01D 53/96* | (2006.01) | |
| *B01D 53/72* | (2006.01) | |
| *B01D 47/14* | (2006.01) | |
| *B01D 53/62* | (2006.01) | |
| *B01D 1/00* | (2006.01) | |

(52) U.S. Cl.
CPC ......... *B01D 47/14* (2013.01); *B01D 53/1493* (2013.01); *B01D 53/346* (2013.01); *B01D 53/62* (2013.01); *B01D 53/72* (2013.01); *B01D 53/96* (2013.01); *B01D 2247/14* (2013.01); *B01D 2251/10* (2013.01); *B01D 2251/304* (2013.01); *B01D 2251/306* (2013.01); *B01D 2251/404* (2013.01); *B01D 2257/104* (2013.01); *B01D 2257/504* (2013.01); *B01D 2257/7022* (2013.01); *Y02C 20/40* (2020.08); *Y02P 70/10* (2015.11)

(58) Field of Classification Search
CPC .. B01D 47/14; B01D 53/96; B01D 2257/504; B01D 2257/104; B01D 2251/404; B01D 2251/306; B01D 2251/10; B01D 2251/304; B01D 2257/7022; B01D 2247/14; A23B 7/144; A61L 9/145; Y02P 70/34; Y02C 10/04
USPC ........................................................ 426/320
See application file for complete search history.

(56) References Cited

U.S. PATENT DOCUMENTS

| | | | |
|---|---|---|---|
| 2009/0100674 A1 | 4/2009 | Sorenson et al. | |
| 2014/0050831 A1 | 2/2014 | Itzhak | |
| 2014/0200137 A1 | 7/2014 | Forsythe et al. | |
| 2016/0030615 A1* | 2/2016 | Sardo | ............... A61L 9/122 422/28 |

FOREIGN PATENT DOCUMENTS

| | | | | |
|---|---|---|---|---|
| EP | 0452512 A1 * | 10/1991 | ........... A23L 3/3409 | |
| EP | 2918336 A1 | 9/2015 | | |
| FR | 1338080 A | 9/1963 | | |
| FR | 2441812 A1 | 6/1980 | | |
| FR | 2964887 A1 | 3/2012 | | |
| FR | 2992225 A1 | 12/2013 | | |
| GB | 397848 A * | 8/1933 | ............. A23B 7/148 | |
| GB | 397878 A | 8/1933 | | |
| GB | 476272 A | 12/1937 | | |
| GB | 782848 A | 9/1957 | | |
| GB | 1054405 A | 1/1967 | | |
| JP | S47-038978 B | 10/1972 | | |
| JP | S49-041891 Y1 | 11/1974 | | |
| JP | H05-137502 A | 6/1993 | | |
| JP | H08-256679 A | 10/1996 | | |
| RU | 2138939 C1 | 10/1999 | | |
| TW | 201101993 A | 1/2011 | | |
| WO | 00/32063 A1 | 6/2000 | | |
| WO | 2007/026363 A2 | 3/2007 | | |
| WO | 2007/026363 A3 | 6/2007 | | |
| WO | 2012/081015 A1 | 6/2012 | | |
| WO | 2014/001201 A1 | 1/2014 | | |
| WO | 2017/042072 A1 | 3/2017 | | |
| WO | 2017/220587 A1 | 12/2017 | | |

OTHER PUBLICATIONS

Search Report in FR Application No. 1655717 dated Oct. 26, 2016 in 2 pages.
Office Action dated Dec. 6, 2022 of divisional U.S. Appl. No. 17/025,672.

* cited by examiner

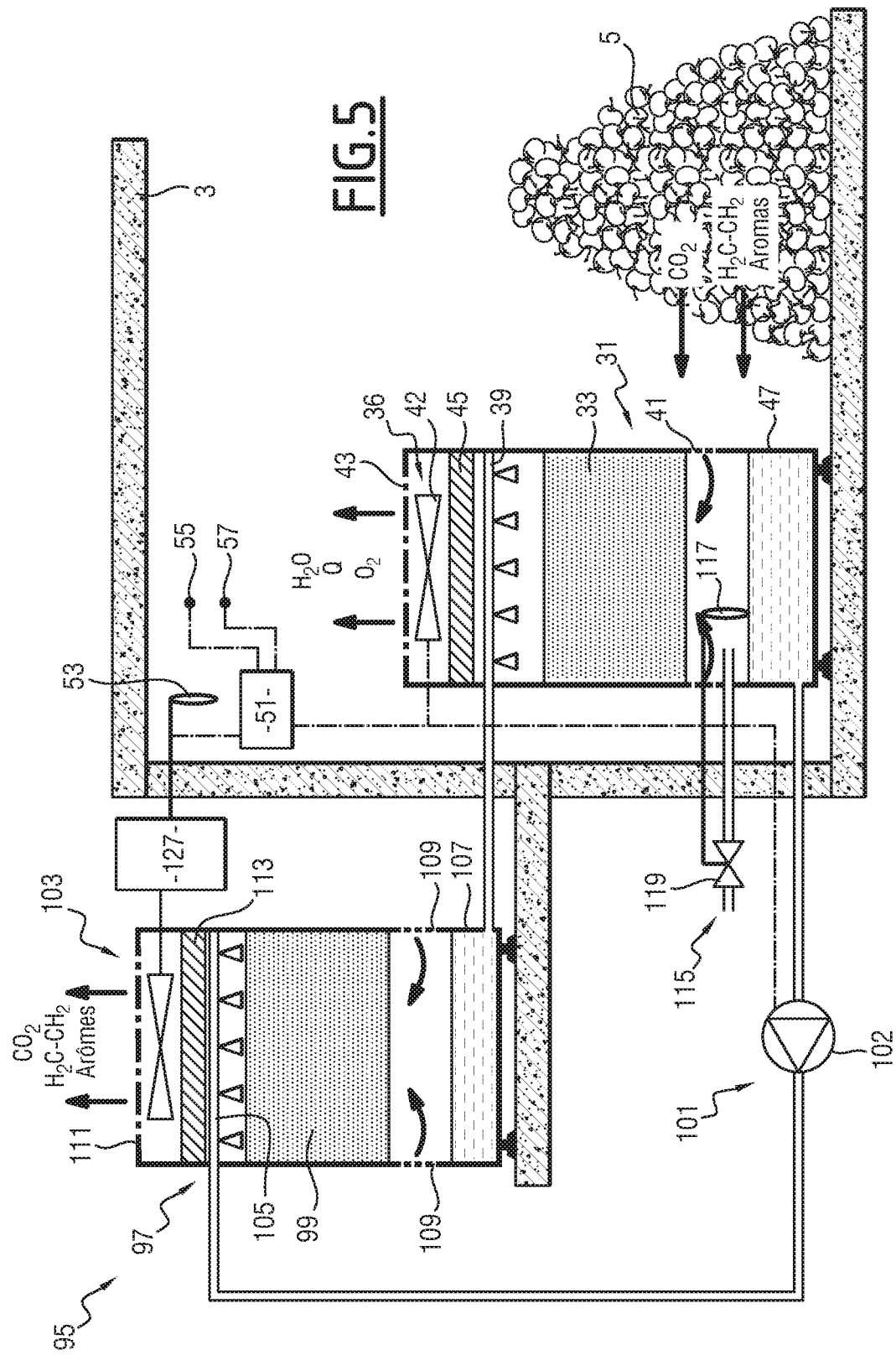

METHOD AND ASSEMBLY FOR THE TREATMENT OF THE ATMOSPHERE IN A STORAGE SPACE FOR VEGETABLE PRODUCTS

FIELD

The invention generally relates to the preservation of vegetable products stored in large volume chambers.

More specifically, according to a first aspect, the invention relates to a method for treating the atmosphere of a storage of vegetable products having a volume greater than 200 m$^3$.

BACKGROUND

It is necessary to manage a large number of parameters in order to control the process of maturation of stored vegetable products.

The respiration of the preserved vegetable products depends on the plant variety, their state of maturation, the storage temperature and the composition of the atmosphere.

Vegetable products absorb oxygen and produce carbon dioxide, aromas and ethylene. Through a chain reaction, the ethylene product accelerates the maturation process. The concentration of these different gases in the atmosphere has to be managed.

In addition, it is necessary to maintain sufficient humidity inside the storage.

In addition, the vegetable products are typically treated by injecting safeners into the atmosphere, which are intended to improve the preservation of vegetable products.

SUMMARY

In this context, the invention aims to provide a method that makes it possible to perform one or more of the above functions in an efficient manner.

To this end, the invention relates to a method for treating the atmosphere of a vegetable product storage having a volume greater than 200 m$^3$, wherein the method comprises at least one step of bringing the atmosphere into contact with a liquid flow by circulation in a packing.

In addition, the method may have one or more of the following features considered individually or in any technically feasible combination:
- the liquid comprises at least one volatile biocidal and/or safener product with a boiling temperature between 60 and 280° C., wherein the liquid is evaporated at the contacting step at a temperature below 50° C.;
- the liquid is water, and the contacting step aims to remove dust and aromas from the atmosphere;
- the liquid contains at least one additive, and the contacting step aims at removing $CO_2$ and/or ethylene from the atmosphere;
- the at least one additive comprises an oxidant, for example permanganate or dichromate;
- the method comprises, after the contacting step, another step of contacting the atmosphere with at least one other liquid flow by circulation in another packing, wherein the other liquid comprises at least one volatile biocidal and/or safener product with a boiling point between 60 and 280° C., wherein the other liquid is evaporated at the other contacting step at a temperature below 50° C.;
- the method comprises a step of measuring the concentration of the volatile biocidal and/or safener product in the atmosphere, wherein the flow rate of the other liquid flow to the contacting step, is adjusted according to the measured concentration;

the method comprises:
- a step of collecting the liquid flow resulting from the contacting step;
- a step of regenerating the liquid flow resulting from the contacting step, during which the liquid flow is brought into contact with an air flow from outside the storage by circulation in an external packing, wherein the liquid flow is then reused in the contacting step;
- the method comprises a step of measuring the concentration of $CO_2$ and/or $O_2$ in the storage atmosphere, wherein the flow rate of the liquid flow is adjusted as a function of the measured concentration;
- the method comprises a step of measuring the temperature and/or the humidity in the storage atmosphere, wherein a flow rate of the atmosphere at the contacting step is adjusted as a function of the temperature and/or humidity measured; and
- the method comprises a step of measuring the temperature in the storage atmosphere, wherein a flow rate of the outer air flow at the regeneration step is adjusted at least as a function of the measured temperature.

According to a second aspect, the invention relates to a unit for treatment of the atmosphere of a storage of vegetable products having a volume greater than 200 m$^3$, wherein the unit comprises at least:
- a contacting device comprising a packing;
- a device for injecting a liquid flow into the contacting device;
- a device for circulating the storage atmosphere in the contacting device; wherein the contacting device is so designed that the atmosphere is brought into contact with the liquid flow by circulation in the packing.

According to a third aspect, the invention relates to a system comprising a storage of vegetable products having a volume greater than 200 m$^3$, and a unit for treatment of the atmosphere of the storage having the above characteristics. The storage advantageously contains a quantity of vegetable products.

The unit may also have one or more of the following features, considered individually or in any technically feasible combination:
- the contacting device comprises a reservoir and a dose of liquid stored in the reservoir, wherein the liquid comprises at least one volatile biocidal and/or safener product with a boiling point between 60 and 280° C., wherein the liquid is evaporated in the contacting device at a temperature below 50° C.;
- the liquid is water, while the contacting device is designed to eliminate the dust and the aromas from the atmosphere;
- the liquid contains at least one additive, while the contacting device is designed to remove $CO_2$ and/or ethylene from the atmosphere;
- the unit comprises:
    another contacting device comprising another packing;
    a device for injecting a flow of another liquid into the other contacting device;
    a device designed to circulate the atmosphere exiting the contacting device in the other contacting device; wherein the other contacting device is so designed that the atmosphere is brought into contact with the other liquid flow by circulation in the other packing; wherein the other contacting device comprises another reservoir and a dose of the other liquid stored in the other reservoir, wherein the other liquid comprises at least one volatile biocidal and/or safener product with a boiling point between 60 and 280° C., while the other liquid is evaporated in the other contacting device at a temperature below 50° C.;

the unit comprises a device for regenerating the liquid flow, with:

an external contacting device, comprising an outer packing;

a device for injecting the liquid flow coming from the contacting device into the external contacting device;

a device for circulating an air flow from outside the storage (3) in the external contacting device; wherein the external contacting device is so designed that the liquid flow is brought into contact with an air flow from outside the storage by circulation in the outer packing and then recycled in the contacting device.

BRIEF DESCRIPTION OF THE DRAWINGS

Other features and advantages of the invention will become apparent from the detailed description given below, for information only and in no way limitative, with reference to the appended figures, wherein:

FIG. 5 shows a simplified schematic representation of a fourth embodiment of the invention.

DETAILED DESCRIPTION

Figure 1:
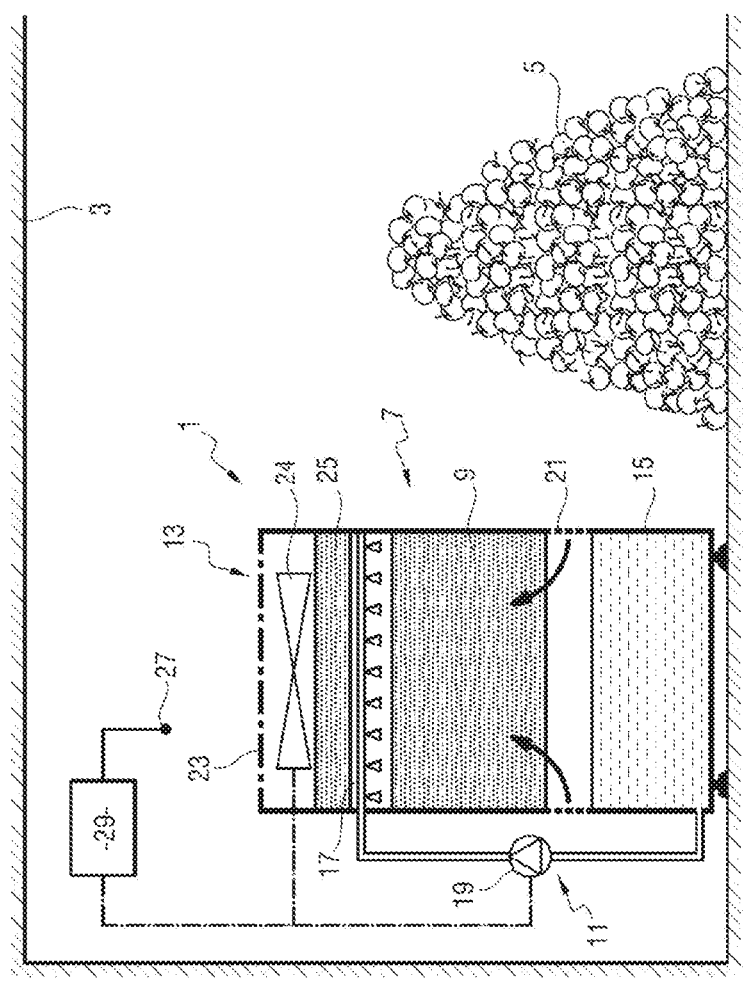
FIG. 1 shows a simplified schematic representation of a first embodiment of the invention.

The unit 1 illustrated in the figures and the corresponding method, are intended for the treatment of the atmosphere of a storage 3 for vegetable products 5 having a volume greater than 200 m$^3$.

Thus, the unit and the method are intended to be applied to a large volume storage, for example a chamber, a silo, a greenhouse or any other premises for the storage of vegetable products. The storage is a closed enclosure, in the sense that exchanges between the storage atmosphere and the outside, in particular gas exchanges, are very reduced in order to avoid jeopardizing the preservation of vegetable products.

Vegetable products are typically fruits or vegetables, which are stored after harvesting and before shipment to retailers.

The storage volume is typically greater than 200 m$^3$, preferably greater than 500 m$^3$ and more preferably greater than 1000 m$^3$.

The unit 1 comprises at least:

a contacting device comprising a packing;

an injection member for a liquid flow in the contacting device;

a member for circulating the storage atmosphere in the contacting device.

The contacting device is so designed that the atmosphere is brought into contact with the liquid flow by circulation in the packing.

The corresponding method comprises at least one step of contacting the atmosphere with a liquid flow by circulation in a packing.

The contacting is performed in any type of device containing the packing. For example, it may be performed in a packed tower.

The term "packing" here refers to any type of structure that makes it possible to obtain a large contact surface between a liquid phase and a gaseous phase, and thus improve the exchanges between the liquid phase and the gaseous phase.

The packing may thus be a loose type packing or a structured type packing.

In the present case, the packing is, for example, of the Raschig ring or Pall ring type, or a honeycomb structured packing.

It is typically made of a plastic material.

The contacting makes it possible to carry out particularly effective transfers between the liquid flow and the atmosphere of the storage.

As will be described below, these transfers serve different purposes, depending on the nature of the liquid:

filtration of the atmosphere, in particular the trapping of dust and suspended soil in the atmosphere;

humidification of the atmosphere;

elimination of $CO_2$ released by vegetable products;

elimination of ethylene ($C_2H_4$) released by vegetable products;

elimination of aromas released by vegetable products;

reintegration of oxygen consumed by vegetable products;

sterilization of the atmosphere;

application of a protective treatment for vegetable products.

The storage atmosphere here corresponds to the volume of gas filling the storage and bathing the vegetable products.

This atmosphere typically comprises air plus gases and products released by vegetable products as they mature. It also comprises water vapor.

Alternatively, the atmosphere may be a modified atmosphere, for example depleted of oxygen. This is particularly the case for the storage of certain vegetable products such as apples.

According to a first embodiment illustrated in FIG. 1, the liquid used comprises at least one volatile biocidal and/or safener product with a boiling point between 60 and 280° C., wherein the liquid is evaporated at the contacting step at a temperature below 50° C.

When the product is a biocidal product, the treatment aims to sanitize the storage. Typically, this treatment is applied when the storage does not contain vegetable products.

When the product is a safener product, which may also be called a phytosanitary product, the treatment aims to protect vegetable products by preventing the development of diseases and/or rotting.

The liquid contains only biocidal products, or phytosanitary products, or comprises one or more biocidal products mixed with one or more phytosanitary products.

At least one of the phytosanitary products is chosen from the following list: essential oil, terpenes, saturated or unsaturated C3 to C9 alcohol, for example isopropanol, isooctanol, 2-ethylhexanol, volatile synthetic products such as glutaraldehyde, hexanal, dimethylnaphthalene and 3-decene-2-one.

The essential oil is, for example, selected from the group consisting of mint oil, clove oil, rose oil, thyme oil, oregano oil. Alternatively, the liquid may comprise one of the constituents of these oils, selected from the group consisting of L-carvone, eugenol, geraniol, thymol, carvacrol.

For a disinfection application, the biocidal product is a volatile product, natural or synthetic, having biocidal properties, such as clove oil, thyme oil, geraniol, ethyl alcohol, glutaraldehyde.

Typically, the liquid only comprises products without solvent or adjuvant. Alternatively, the liquid may comprise an aqueous or organic solvent, in which is dissolved the products and one or more adjuvants. The aqueous solvent is, for example, water. The organic solvent is, for example, a solvent of the type described in FR 2 791 910, or glycols, di-glycols and their relative esters. The adjuvants are, for example, substances capable of transporting the active substances, or capable of giving a dilution effect.

In any event, the liquid during the contacting step is vaporized at a temperature below 50° C., preferably below 20° C., in particular between −2° C. and +12° C., and, in particular, between 0 and 10° C. For example, the liquid is evaporated at room temperature.

As illustrated in FIG. 1, the processing unit 1 comprises:
the contacting device 7 comprising a packing 9;
the device 11 for injecting the liquid flow into the contacting device 7;
the device 13 for circulating the storage atmosphere in the contacting device 7.

The contacting device 7 is so designed that the atmosphere is brought into contact with the liquid flow by circulation in the packing 9. Typically, the contacting device 7 is a packed tower, which has a vertical axis in the example shown.

The injection device 11 comprises a reservoir 15 of liquid, and a dose of liquid stored in the reservoir 15. The reservoir 15 is typically a tank, placed vertically under the packing 9.

The injection device 11 is arranged to inject the liquid above the packing 9.

For this purpose, it typically comprises one or more sprinklers 17, for example ramps, placed above the packing, and a transfer member 19, such as a pump, sucking the liquid into the reservoir 15 and discharging this in the member(s) 17.

The circulation device 13 is arranged to create an upward circulation of the atmosphere inside the contacting device 7.

To do this, the contacting device 7 comprises one or more inlets 21 for the atmosphere opening inside the contacting device 7, under the packing 9.

Each inlet 21 communicates fluidly with the interior of the storage 3.

The contacting device has an outlet 23 for the atmosphere loaded with evaporated liquid, placed in the upper part of the contacting device, above the packings 9. The outlet 23 is fluidly connected with the interior of the storage 3.

The circulation device 13 comprises, for example, a circulation member 24 such as a fan or a blower, placed above the packing 9, typically at the top of the contacting device 7.

The circulation member 24 draws the atmosphere charged with evaporated liquid over the packing 9, and delivers it at, or towards, the outlet 23.

The packing 9, as specified above, is of any suitable type.

Preferably, the contacting device 1 comprises a droplet separator 25, placed above the sprinklers 17, and more precisely between the sprinklers 17 and the circulation member 24.

In an exemplary embodiment, the contacting device 7 has a square, substantially constant, horizontal section of 700× 700 mm. The reservoir 15 has the same horizontal section, and has a height of between 500 and 700 mm. The device has four inlets 21, each disposed on one side. The packing 9 has a height of about 1 m. The packing is placed, for example, 700 mm below the liquid inlet, while the droplet separator 25 is placed 300 mm above the liquid inlet.

The treatment unit 1 preferably comprises a sensor 27 for measuring the concentration of the volatile biocidal and/or safener product in the atmosphere and an electronic device 29 informed by the sensor 27.

The electronic device 29 is programmed to control the injection device 11 and/or the circulation member 13.

More precisely, it is, in particular, programmed to regulate the flow rate of the liquid flow as a function of the concentration measured by the sensor 27. Preferably, it also controls the circulation member 24.

The electronic device 29 is, for example, a calculator or a computer part. Alternatively, the electronic control device 29 may be implemented in the form of Field Programmable Get Arrays (FPGAs) or in the form of an Application Specific Integrated Circuit (ASIC). The electronic device 29 is programmed to implement a treatment strategy.

The treatment strategy may be of any type. As described in the French application filed on the same day as the present patent application, the treatment may be spread over a long period of time, in order to inject the product gradually in a small quantity, and in order to maintain the concentration of products inside the storage constantly at a moderate level.

Conversely, it is possible to perform treatment aimed at rapidly obtaining the concentration of saturation of the product in the atmosphere, over a short period. This makes it possible, for example, to obtain the sterilization of the empty or partially empty storage. Rather than maintain a lower concentration of active products in this case for a long time, the aim is, on the contrary, to perfectly sterilize the storage by saturating the atmosphere very quickly, wherein the vapor of the product thus acts immediately and optimally in all parts of the premises.

This effect may be obtained because the contact surface between the liquid and the atmosphere is high as a result of the presence of the packings. The machine sold under the name XEDAVAP®, whose principle is to inject the liquid to be evaporated on a canvas swept by a current of air, has a maximum developed canvas surface of about 4 m². This allows the evaporation, for example, of 1.2 liter/day of mint oil.

On the contrary, the treatment unit of the present invention provides a contact area between the gas and the liquid which may be, for example, up to 70 m². It is thus possible to evaporate much larger quantities of products, for example 20 liters of product per day, and to reach the saturation concentration of the product in the atmosphere more quickly.

The operation of the unit is as follows.

The liquid to be evaporated is disposed in the reservoir 15. The transfer member 19 delivers the liquid into the sprinkler member(s) 17, which project(s) the liquid towards the packing 9. The member 24 for circulation of the atmosphere creates an ascending gas flow. The atmosphere enters the device 7 through the inlets 21, flows upwards through the packing 9. The liquid flows downwards through the packing 9, wherein a part of the liquid is evaporated upon contact with the gas flow and is drawn with the atmosphere in the form of vapor. The fraction of the liquid that is not evaporated falls back into the reservoir 15. It is recycled. The atmosphere loaded with evaporated liquid passes through the droplet separator 25 and is discharged by the circulation member 24 to the outlet 23.

The unit 1 is typically placed inside the storage. It thus sucks the storage atmosphere directly through the inlet(s) 21, and discharges this atmosphere loaded with vapor directly into the storage via the outlet 23.

The liquid flow rate is for example 3 m³/hour, and the flow rate of the atmosphere is about 2000 m³/hour.

The treatment method according to the first embodiment comprises a step of contacting the atmosphere of the storage 3 with at least one liquid flow by circulation in another packing, wherein the liquid comprises at least one volatile biocidal and/or safener product with a boiling temperature between 60 and 280° C., wherein the liquid is evaporated in the other contacting step at a temperature below 50° C.

Typically, the method comprises a step of measuring the concentration of the volatile biocidal and/or safener product in the atmosphere, while the flow rate of the liquid flow at the contacting step is adjusted as a function of the measured concentration.

Preferably, the injected liquid is collected in a reservoir under the packing and recycled to the contacting step.

The method is intended to be implemented by the treatment unit 1 described above. Conversely, the treatment unit 1 described above is particularly suitable for implementing the method.

A second embodiment of the invention will now be described with reference to FIG. 2. Only the points by which this second embodiment differs from the first embodiment will be detailed below.

In the second embodiment, the liquid is water, and the contacting is intended to remove dust and aromas from the atmosphere. The aromas are released by the vegetable products during their maturation.

As in the first embodiment, the unit 1 comprises:
a contacting device 31 comprising a packing 33;
a device 35 for injecting the liquid flow into the contacting device 31;
a device 36 for circulating the atmosphere in the contacting device 31.

The injection device 35 comprises a water inlet 37, feeding one or more sprinklers 39 such as ramps. The water inlet 35 is typically connected to a water distribution network, or a water tank. Water is typically pure water, with no additives. The water is at a temperature below 50° C., typically at room temperature.

The circulation device 36 is arranged to create an upward circulation of the atmosphere inside the contacting device 31.

To do this, the contacting device 31 comprises one or more inlets 41 for the atmosphere and that open under the packing 33 inside the contacting device 31. The circulation device 36 comprises a circulation member 42, for example a fan or a blower, placed above the packing 33, and discharging the atmosphere at an outlet 43 communicating fluidly with the inside of the storage. A droplet separator 45 is interposed vertically between the sprinkler member(s) 39 and the circulation member 42.

The contacting device 35 further comprises a tank 47 placed under the packing 33, and designed to collect the water which is not evaporated in contact with the atmosphere in the packing 33. The collection tank 47 has an outlet 49 typically connected to a sewer.

Thus, the wastewater containing the undesirable products, i.e. at least the dusts and aromas, is discharged from the contacting device 7 to the sewers. It is not recycled.

Alternatively, the water may be recycled after being purified.

As in the first embodiment, an electronic device 51 controls the circulation member 42 and the injection device 35.

Typically, the treatment unit is operated periodically, for example once a day, in order to sanitize the storage atmosphere.

The flow rate of water is typically between 300 and 500 liters/hour, while the flow rate of the atmosphere through the packing is of the order of 2000 m³/hour.

It should be noted that the device and the method according to the second embodiment, in addition to trapping the dust and eliminating the aromas, make it possible to humidify the atmosphere of the storage 3, and also, where appropriate, to enrich the oxygen atmosphere.

In fact, as specified above, it is generally necessary to maintain a certain level of moisture in the storage atmosphere in order to prevent the vegetable products from drying out and getting a wrinkled appearance.

When the storage is equipped with an air conditioning device that is intended to maintain the temperature inside the storage within a predetermined range, there is a production of condensation of the water vapor contained in the atmosphere, in particular at the level of the heat exchangers or condensers of the air conditioning device.

The liquid circulating in the contacting device is partially evaporated, which at least partially offsets the condensed water vapor in the air conditioner.

In addition, vegetable products stored in a storage consume oxygen from the atmosphere through their natural respiration. It is therefore necessary to re-enrich the oxygen atmosphere regularly. In the present case, particularly in the second embodiment, the water supplying the contacting device contains dissolved oxygen, which is partially vaporized when coming into contact with the atmosphere.

Preferably, the unit 1 comprises a sensor 53 to measure the temperature inside the storage 3. The electronic device 51 is designed to adjust the flow rate of the liquid flow and/or the flow rate of the atmosphere at least as a function of the measured temperature.

Advantageously, the unit 1 comprises a sensor 55, that is designed to analyze the concentration of $O_2$ in the storage atmosphere, typically a gas analyzer. The electronic device 51 is designed to adjust the flow rate of the liquid flow at least as a function of the measured concentration.

For example, the unit 1 comprises a hygrometer 57 that is arranged to measure the humidity of the atmosphere in the chamber 3. The electronic device 51 is programmed to adjust the flow rate of the atmosphere and/or the flow rate of the liquid flow at least as a function of the humidity measured by the hygrometer 57.

According to a variant of the second embodiment, the liquid placed in contact with the storage atmosphere contains at least one additive, while the contacting device is designed to remove $CO_2$ and/or ethylene from the storage atmosphere.

Thus, the liquid comprises water plus an additive dissolved in water. To remove the $CO_2$, the additive is, for example, sodium hydroxide (NaOH), potassium hydroxide (KOH), quicklime or slaked lime (CaO, Ca(OH)$_2$).

To remove ethylene, the additive contains a strong oxidant, for example permanganate ($MnO^{4-}$) or dichromate ($Cr_2O_7^{2-}$). Typically, the additive contains sodium permanganate or potassium permanganate or potassium dichromate.

The liquid may contain only one additive to remove $CO_2$, or only one additive to remove ethylene, or contain one additive to remove $CO_2$ and one additive to remove ethylene.

The concentration of the various additives is chosen according to the amount of $CO_2$ and the amount of ethylene to be removed.

For example, the liquid may be an aqueous solution of sodium permanganate or potassium permanganate, saturated with permanganate.

As mentioned above, $CO_2$ and ethylene are released by vegetable products as they mature.

Thus, in the variant of the second embodiment of the invention, the device and the method make it possible to eliminate dust, aromas, $CO_2$ and/or ethylene from the atmosphere. They also re-humidify the atmosphere and re-enrich the atmosphere with $O_2$ in water.

In this case, the sensor 55 is preferably designed to analyze the concentration(s) of $CO_2$ and/or ethylene in the storage atmosphere. The electronic device 51 is designed to adjust the flow rate of the liquid flow as a function of the concentration(s) measured.

The method for treating the storage atmosphere according to the second embodiment thus comprises a step of contacting the atmosphere with a liquid flow by circulation in a packing, wherein the liquid is water that optionally contains an additive.

Typically, the method comprises a step of measuring the concentration(s) of $O_2$ and/or $CO_2$ and/or ethylene in the atmosphere, and/or measuring the temperature of the atmosphere, and/or measuring the humidity in the storage atmosphere, wherein the flow rate of the liquid flow and/or the flow rate of the atmosphere at the contacting step is adjusted as a function of the measurement(s).

Preferably, the injected liquid is collected under the packing and then discharged to the sewers. It is not recycled.

The method is intended to be implemented by the processing unit 1 described above. Conversely, the processing unit 1 described above is particularly suitable for implementing the method.

Another variant of the second embodiment will now be described, with reference to FIG. 3. Only the points by which this variant differs from that of FIG. 2 will be detailed below. Identical elements and those providing the same function will be designated by the same reference.

In this alternative embodiment, the device and the method of the invention are mainly aimed at removing ethylene from the storage atmosphere.

The injection device 35, in addition to the sprinkler member(s) 39, comprises a transfer member 58 such as a pump that sucks the liquid from the tank 47 and drives it into the sprinkler member(s) 39.

To remove ethylene, the liquid comprises an additive containing a strong oxidant such as permanganate ($MnO^{4-}$) or dichromate ($Cr_2O_7^{2-}$). Typically, the additive contains sodium permanganate or potassium permanganate or potassium dichromate.

Alternatively, the liquid has one or more additional additives. For example, the liquid may comprise a metal salt to increase the rate of reaction of the oxidant with ethylene (catalyst). This catalyst is typically iron sulfate when the oxidant is potassium permanganate. In another example, the additional additive is provided for removing $CO_2$.

For example, the liquid is an aqueous solution of sodium permanganate or potassium permanganate, supersaturated with permanganate. In other words, for a tank 47 containing a given volume of water V, a mass of permanganate M greater than $C_{sat} \times V$ is initially mixed with water, wherein $C_{sat}$ is the saturation concentration of the permanganate in water. Part of the permanganate is not dissolved initially and remains in the form of solid $MnO_2$ dioxide in the tank 47.

Then, as the device operates, the permanganate dissolved in water is consumed by reaction with ethylene contained in the storage atmosphere. A fraction of the solid $MnO_2$ dioxide passes into solution, so that the concentration of permanganate remains at the saturation concentration. For example, the initial mass of permanganate is chosen so that the device may be used throughout the storage period without having to change the liquid. At the end of the storage period, the liquid is sent to a manganese salt recovery center.

The tank 47 typically contains between 1 $m^3$ and 3 $m^3$ of liquid, as a function of the size of the storage chamber and the treatment capacity of the device/process. For example 150 kg of permanganate is initially mixed for 2 $m^3$ of liquid. Approximately 60 kg of permanganate will be dissolved, while the remaining 90 kg constitutes a reservoir to maintain the saturation permanganate concentration during the storage period.

Draining 59 allows the liquid contained in tank 47 to be discharged to the sewers, typically when the concentration of permanganate has decreased excessively. The wastewater containing the undesirable products is thus periodically discharged to the sewers from the contacting device 31. The draining 59 is normally stopped by a valve 61. Means (not shown) are provided to fill the tank 47 with fresh liquid.

Typically, the treatment unit is operated periodically, for example once a day, in order to sanitize the storage atmosphere.

The liquid flow rate is typically between 5 and 50 $m^3$/hour, while the flow rate of the atmosphere through the packing is between 1 and 10 volume/hour, i.e. between 2000 and 20000 $m^3$/hour for a volume to be treated of 2000 $m^3$.

The velocity of the air in the packing must ensure intimate contact with the liquid, in order to ensure the complete oxidation of the ethylene. The flow rates of liquid and air are therefore chosen according to the cross-section of the packing, in order to achieve this contact and ensure a very high air flow, which allows the ethylene concentration in the chamber to be maintained at an extremely low level. On the other hand, the velocity of the air should remain lower than 3.5 m/sec in order to avoid the entrainment of liquid droplets.

For example, for chambers up to 2000 $m^3$, the air flow is of the order of 10,000 $m^3$/h and the packing has a cross-section of 0.9 m×1.2 m, i.e. an air speed of 2.57 m/sec approx.

For chambers between 2000 $m^3$ and 4000 $m^3$, the packing section is, for example, 1.2 m×1.2 m, and the air flow is 16,000 $m^3$/h, or 3.09 m/sec.

Advantageously, the unit 1 comprises a sensor 63 that is designed to analyze the ethylene concentration in the storage atmosphere, typically a gas analyzer. The electronic device 51 is designed to adjust the flow rate of the liquid flow as a function of the measured concentration.

It should be noted that the present variant embodiment, as described above, also makes it possible to eliminate the dust, the aromas, and possibly the $CO_2$ from the atmosphere. It also helps to re-humidify the atmosphere and helps control the temperature of the atmosphere.

Preferably, the unit 1 then comprises a sensor 53 for measuring the temperature inside the storage 3, and/or a sensor 55 that is designed to analyze the concentration(s) of $O_2$ and/or ethylene in the atmosphere of the storage, and/or a hygrometer 57 that is arranged to measure the humidity of the atmosphere in the chamber 3. The electronic device 51 is designed to adjust the flow rate of the liquid flow and/or the flow rate of the atmosphere as a function of measurements returned by the sensors 53, 55, 57 and 63.

The method for treating the storage atmosphere according to the other variant of the second embodiment thus comprises a step of contacting the atmosphere with a liquid flow by circulation in a packing, wherein the liquid contains at least one additive as described above.

Typically, the method comprises a step of measuring the concentration(s) of $O_2$ and/or $CO_2$ and/or ethylene in the atmosphere, and/or measuring the temperature of the atmosphere, and/or measuring the moisture in the storage atmosphere, wherein the flow rate of the liquid flow and/or the flow rate of the atmosphere at the contacting step is adjusted as a function of the measurement(s).

Preferably, the injected liquid is collected under the packing and recycled to the contacting step.

The method is intended to be implemented by the processing unit 1 described above. Conversely, the processing unit 1 described above is particularly suitable for implementing the method.

Figure 2:
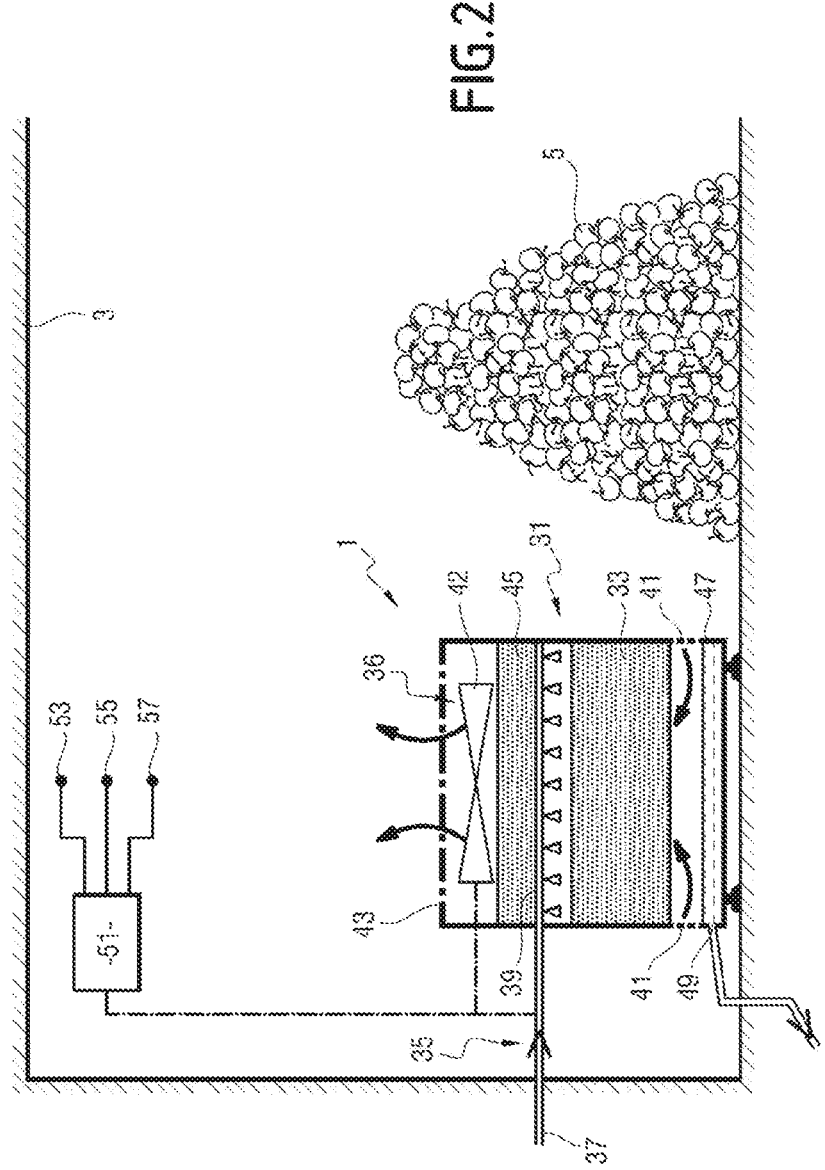
FIG. 2 shows a simplified schematic representation of a second embodiment of the invention.
Figure 3:
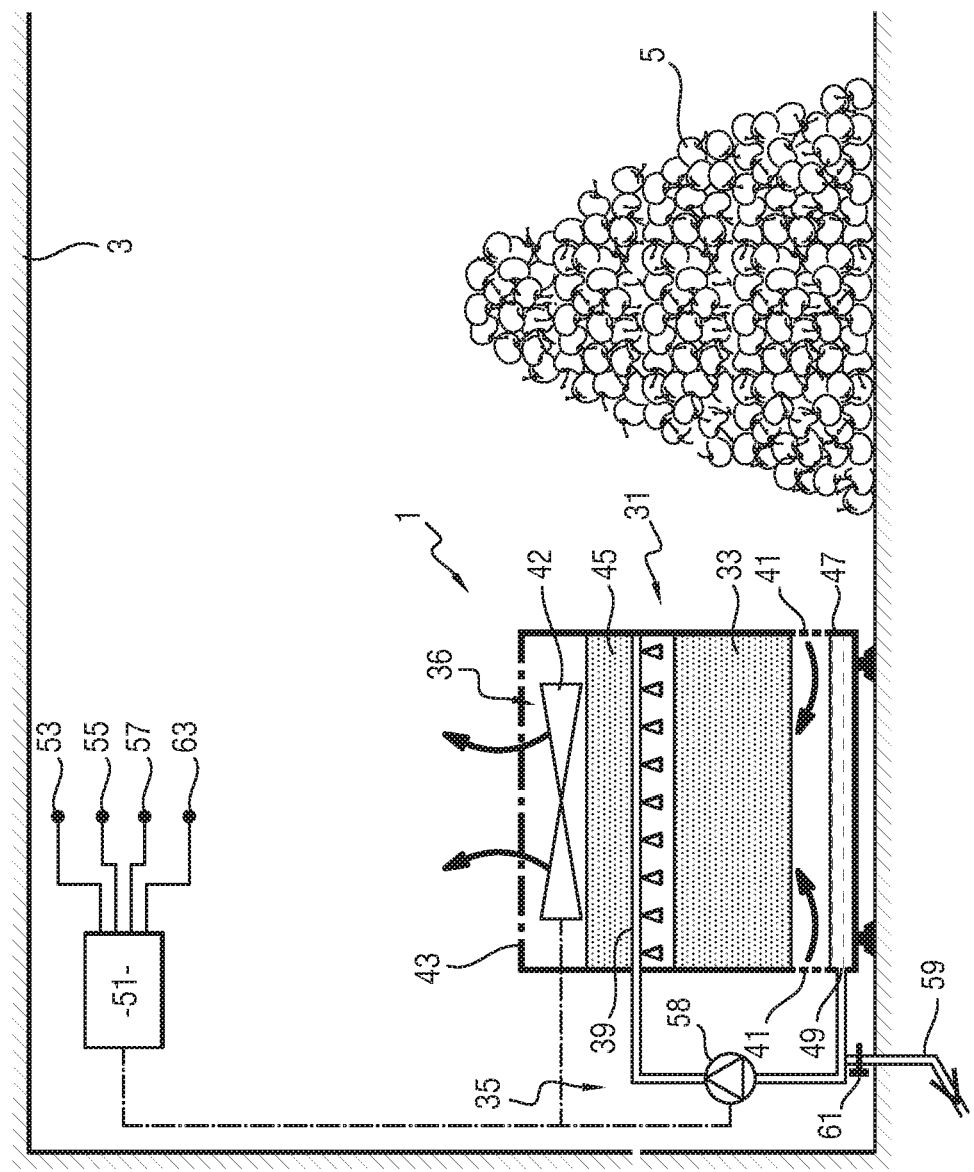
FIG. 3 shows a variant of the second embodiment of the invention.

It should be noted that the liquid may not be recycled, but rather drained directly from the tank 47, as shown in FIG. 2, after a single pass through the contacting device.

The invention makes it possible to maintain the ethylene content in the storage atmosphere at extremely low values, less than 1 ppm.

The methods currently used for this purpose have important drawbacks.

One existing method is to block ethylene receptors in stored plants. These plants then stop producing ethylene. 1-MCP (1-methylcyclopropene) is typically used for this purpose. The disadvantage of this method is that the development of plants is permanently blocked, and they can not mature normally.

Other methods consist in destroying the ethylene molecules in the atmosphere, either by chemical oxidation or by catalytic combustion. These methods do not permit the treatment of sufficient airflows to reduce the ethylene concentration to less than 1 ppm in large volume storage facilities of at least 200 m$^3$.

Such a rate contributes to significantly slowing the maturation of stored plants. Plants are better preserved and a greater proportion of them are therefore suitable for marketing at the time of opening of the storage. Decay losses are reduced. The development of physiological diseases caused by the development of stored plants is slowed down or prevented. The absence of senescent products promotes preservation. On the other hand, if the absorption of ethylene is interrupted, the plants resume the normal course of their maturation.

A third embodiment of the invention will now be described, with reference to FIG. 4. The elements that are identical or that perform the same functions as in the first two embodiments will be designated by the same references.

In the third embodiment, the unit 1 comprises the contacting device 31 and the injection device 35 of the second embodiment.

It also comprises another contacting device and another device for injecting a liquid, corresponding to those of the first embodiment, designated here by references 7 and 11 as in the first embodiment.

The unit 1 further comprises a device 85 designed to circulate the atmosphere exiting the contacting device 31 in the other contacting device 11.

The atmosphere leaving the device 31 is thus brought into contact with the other liquid flow by circulation in the packing 9.

The liquid injected into the packing 33 is water, possibly with one or more additives as described above for trapping the $CO_2$ and/or the ethylene. The water is at a temperature below 50° C., typically at room temperature.

The other liquid comprises at least one volatile biocidal and/or safener product with a boiling point between 60 and 280° C., while the other liquid is evaporated in the other contacting device 7 at a temperature below 50° C.

Figure 4:
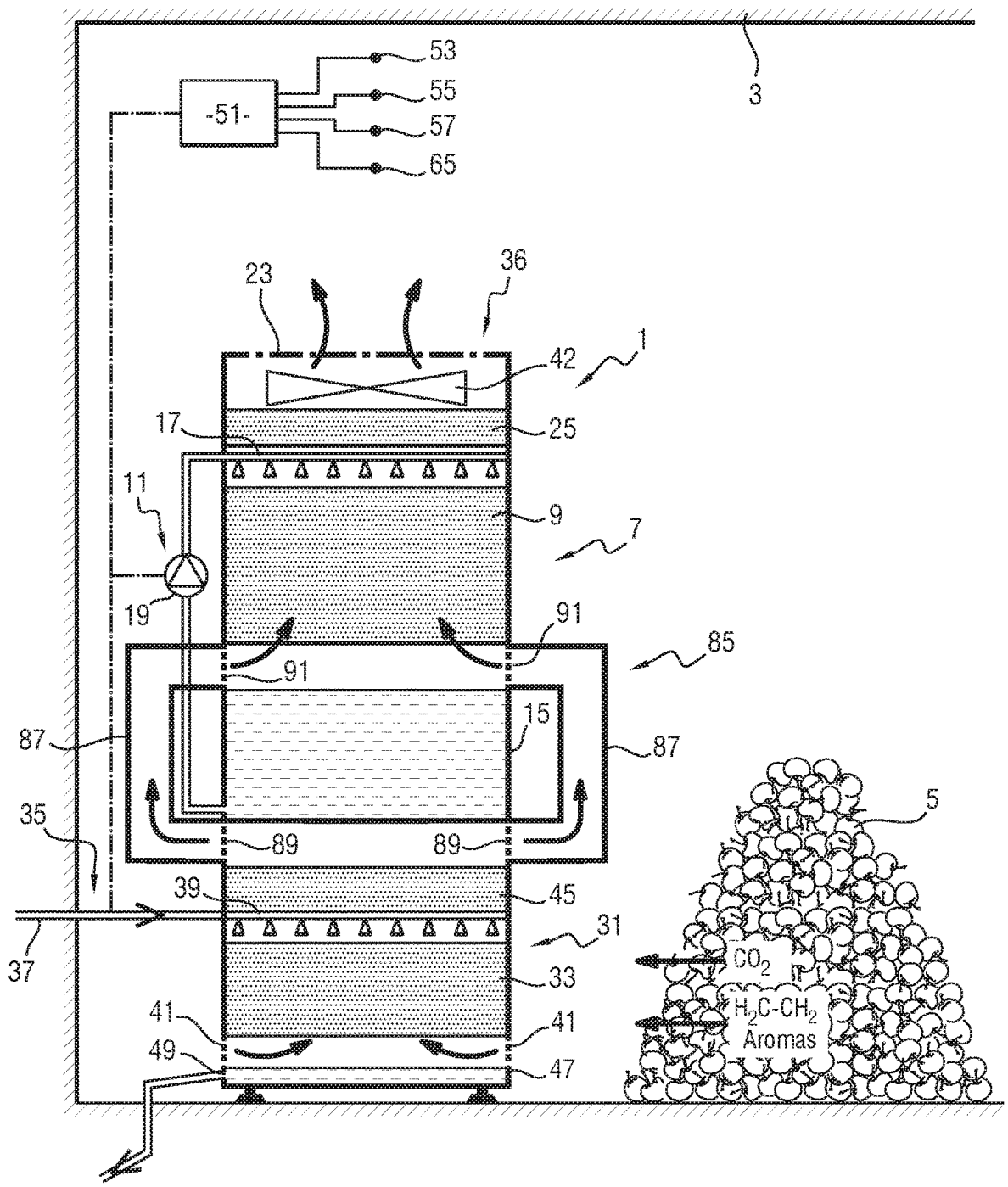
FIG. 4 shows a simplified schematic representation of a third embodiment of the invention.

As may be seen in FIG. 4, the contacting device 31 and the other contacting device 7 are typically stacked one above the other. They form a vertical tower, wherein the contacting device 31 forms the lower part of the tower, while the other contacting device 7 forms the upper part of the tower. Alternatively, they may be arranged in two separate towers.

The unit 1 also comprises a circulation member 42 located at the top of the stack, above the packings of the other contacting device 7. This makes it possible to circulate the atmosphere both through the contacting device 31 and through the other contacting device 7.

The reservoir 15 of the other contacting device is located above the droplet separator 45 of the contacting device.

The device 85, which is designed to circulate the atmosphere exiting the contacting device 31 to the other contacting device 7, comprises one or more passages 87 connecting the outlets 89 of the contacting device to inlets 91 of the other contacting device. The outlets 89 are located vertically between the packing 33 and the reservoir 15, and more precisely vertically between the droplet separator 45 and the reservoir 15. The inlets 91 are located under the packing 9, and more precisely between the reservoir 15 and the packing 9.

The inlets and outlets 89, 91 are provided in the side walls of the tower.

The atmosphere enters the contacting device 31 through the inlets 41 and flows upwards through the packing 33. The liquid arriving through the injection device 35 flows through the packing 33 against the flow in the sense of circulation of the atmosphere. The dust, the aromas, possibly $CO_2$ and/or ethylene, are transferred at least partially from the atmosphere to the liquid during the contacting at the level of the packings 33. The atmosphere then passes through the droplet separator 45, then passes the inlets 89 and circulates in the passages 87 to the inlets 91.

The atmosphere then flows upwards through the packing 9 of the other contacting device. The other liquid, containing the biocidal and/or safener product, is injected by the device 11 above the packing 9. It circulates downwards, and is brought into contact with the purified atmosphere in the packing 9. At least part of the product is transferred from the liquid into the atmosphere. The atmosphere loaded with biocidal and/or safener products leaving the packing 79, flows upwards through the droplet separator and then through the outlet 23 and is discharged in the storage.

The electronic device 51 controls the unit 1 as previously described, with reference to FIGS. 1 and 2. For this purpose, the unit 1 advantageously comprises the temperature sensor 53, the sensor 55 that is designed to analyze the concentration(s) of $O_2$ and/or $CO_2$ and/or ethylene in the storage atmosphere, the hygrometer 57, and a sensor 65 for measuring the concentration of the, or each, product in the atmosphere.

The method for treating the storage atmosphere according to the third embodiment thus comprises:

at least one step of contacting the atmosphere with a liquid flow by circulation in a packing, wherein the liquid is water optionally containing an additive;

after the contacting step, there is another step of contacting the atmosphere with at least one other liquid flow by circulation in another packing, wherein the other liquid comprises at least one volatile biocidal and/or safener product with a boiling temperature between 60 and 280° C., wherein the other liquid is evaporated in the other contacting step at a temperature below 50° C.

When the liquid is water, the contacting step aims to remove only the dust and the aromas from the atmosphere. When the liquid contains an additive such as an alkaline salt, the contacting step also removes $CO_2$ from the atmosphere. When the liquid contains an additive such as permanganate, the contacting step removes ethylene from the atmosphere.

The other contacting step makes it possible to evaporate the, or each, biocidal and/or safener product.

Typically, the method comprises a step of measuring the concentration(s) of $O_2$ and/or $CO_2$ and/or ethylenes and/or the, or each, biocidal and/or safener product in the atmosphere, and/or measuring the temperature of the atmosphere, and/or measuring the humidity in the storage atmosphere, wherein the flow rate of the liquid flow and/or the flow rate of the atmosphere at the contacting step are/is adjusted as a function of the measurement(s).

Preferably, the injected liquid is collected under the packing and then discharged to the sewers. It is not recycled. In contrast, the other injected liquid is typically collected in a reservoir under the other packing and recycled to the other contacting step.

The method is intended to be implemented by the treatment unit 1 described above. Conversely, the treatment unit 1 described above is particularly suitable for implementing the method.

In the third embodiment, the unit 1 has multiple advantages.

In fact, the contacting device 31 makes it possible to eliminate at least the aromas and the dust, and typically also the $CO_2$ and/or the ethylene. The other contacting device 11 makes it possible to evaporate the treatment product.

In the prior art, the $CO_2$ and/or ethylene released by the vegetable products are/is removed by opening the storage doors, in order to at least partially renew the atmosphere inside. This draws the treatment product outside the storage to be dispersed in the atmosphere. Once the doors are closed, it is necessary to spray a large quantity of biocidal and/or safener products in order to restore the concentration of desired products in the atmosphere.

Since the unit 1 eliminates the troublesome products accumulating in the atmosphere, it is no longer necessary to open the doors periodically, so that the consumption of biocidal and/or safener products is accordingly reduced.

A fourth embodiment of the invention will now be described with reference to FIG. 5. Only the points by which this fourth embodiment differs from the second embodiment will be detailed below.

Identical elements or those providing the same functions will be designated by the same references in both embodiments.

In the fourth embodiment, the unit 1 comprises, in addition to the contacting device 31 and the circulation device 36, a device 95 for regenerating the liquid flow.

The regeneration device 95 comprises:
- an external contacting device 97, comprising an outer packing 99;
- a device 101 for injecting the liquid flow coming from the contacting device 31 into the external contacting device 97;
- a device 103 for circulating an air flow from outside the storage in the external contacting device 97.

The external contacting device 97 is so designed that the liquid flow is brought into contact with an air flow from outside the circulation storage in the outer packing 99 in the contacting device 97.

The external contacting device 97 is of the same type as the contacting device 31. This is typically a packed tower.

The device 101 for injecting the liquid flow draws the liquid collected in the tank 47 under the packing 33. It typically comprises a transfer member 102 such as a pump which delivers the liquid to the sprinkling members 105 such as ramps placed above the packing 99. The external contacting device 97 comprises a tray 107 under the outer packing 99 to collect the liquid flowing through the packing 99. This liquid is returned to the sprinkling members 39 of the contacting device 31 by any suitable means, for example by gravity or with a pump (not shown).

The circulation device 103 typically comprises a fan or blower, which creates an upward flow of outside air through the packing 99. The outside air enters the external contacting device 97 through the inlets 109 located under the packing 99. It exits through an outlet 111 located at the top of the external contacting device 97.

This device 97 also comprises a droplet separator 113 situated above the sprinkling members 105.

The contacting device 31 advantageously comprises a supplementary liquid supply 115. This supply 115 is connected to a liquid supply network. The contacting device 31 comprises a liquid level sensor 117 in the tank 47 to control a valve 119 that is placed on the auxiliary power supply 115. The level sensor 117 is so designed that the valve 119 is open when the liquid level in the tray 47 is below a predetermined level, and closed when the level is above a predetermined level.

Preferably, the unit 1 comprises a sensor 53 for measuring the temperature inside the storage 3. The outer air flow at the regeneration step is set at least according to the measured temperature.

This flow is regulated either by a thermostat 127 directly controlling the circulation member 103, or by the control device 51 which is programmed to manage the circulation member 103.

Advantageously, the unit 1 comprises a sensor 55 that is designed to analyze the concentration(s) of $CO_2$ and/or $O_2$ and/or ethylene in the storage atmosphere. The control device 51 is programmed to adjust the flow rate of the liquid flow as a function of the concentration(s) measured.

The control device 51 for this drives the transfer member 102.

For example, the unit 1 comprises a hygrometer 57 that is arranged to measure the humidity of the atmosphere in the chamber 3. The control device 51 is programmed to adjust the flow of the atmosphere at the contacting step as a function of the humidity measured by the hygrometer 57.

Alternatively, the flow rate of the atmosphere at the contacting stage is regulated as a function of the concentration(s) of $CO_2$ and/or ethylene measured by the sensor 55 in the atmosphere of the storage 3.

Each contacting device has a horizontal section of between 0.5 m² and 20 m². Their height is between 2 meters and 6 meters. The liquid flow rate is typically between 20 m³/hour and 1000 m³/hour, wherein the flow rate of the atmosphere in the contacting device 31 is between 2000 and 100000 m³/hour.

The method of treatment according to the fourth embodiment comprises:
- a step of contacting the atmosphere of the storage 3 with the liquid flow by circulation in a packing 33;

a step of collecting the liquid flow resulting from the contacting step;

a step of regenerating the liquid flow resulting from the contacting step, during which the liquid flow is brought into contact with an air flow from outside the storage by circulation in an outer packing 99, wherein the flow liquid is then reused in the contacting step.

The liquid flow is typically a water flow without any additive. In fact, such a system allows work in a closed circuit with a large amount of water, so that the additives intended to remove $CO_2$ and/or ethylene in other embodiments, are not necessary here.

As described above, the method advantageously comprises a step of measuring the concentration(s) of $CO_2$ and/or $O_2$ and/or ethylene in the storage atmosphere, wherein the flow rate of the liquid flow is regulated as a function of the measured concentrations. Similarly, the method advantageously comprises a step of measuring the temperature and/or humidity in the storage atmosphere, wherein the flow rate of the atmosphere at the contacting step is adjusted according to the measured temperature and/or humidity.

Similarly, the method preferably comprises a step of measuring the temperature in the storage atmosphere, wherein the flow rate of the outer air flow at the regeneration step is adjusted at least according to the measured temperature.

In this embodiment, the $CO_2$, ethylene and aromas produced by the respiration of vegetable products stored in the storage are absorbed by the liquid flow at the contacting step. At the same step, the liquid arriving from the outside of the storage is partially vaporized and contributes to maintaining sufficient humidity in the storage atmosphere. In addition, the liquid arrives from the outside with a significant concentration of dissolved oxygen, wherein this oxygen is at least partially released into the storage atmosphere during the step of bringing the liquid into contact with the atmosphere.

Under certain circumstances, depending on the temperature and humidity inside and outside the storage, the contacting step will produce a cooling effect by evaporation of water within the storage. This helps to limit the load on the air conditioning system of the storage 3.

The liquid collected in the tank 47 of the contacting device is directed towards the external contacting device 95. In this device, the aromas, ethylene and $CO_2$ are released into the outside air. The liquid is reoxygenated.

The liquid collected in the tank 107 supplies the contacting device 31.

The method is intended to be implemented by the treatment unit 1 described above. Conversely, the treatment unit 1 described above is particularly suitable for implementing the method.

It is therefore conceivable that the unit and the method according to the fourth embodiment makes it possible to regulate, or at least contributes to regulating, a large number of significant parameters for the preservation and the process of maturation of the vegetable products in the storage. These parameters are the concentration of $CO_2$, and/or ethylene and/or oxygen in the storage atmosphere, the removal of aromas, the humidity in the storage atmosphere, and the temperature inside the storage.

As noted above, this avoids the periodic opening of the storage doors to expel accumulated $CO_2$ by replacing it with fresh outdoor air.

This unit and this method apply, for example, to the storage of potatoes.

In this case, the storage atmosphere is air. The flow rate of the atmosphere in the contacting device 31 is adjusted according to the humidity measured by the hygrometer in the atmosphere of the chamber. The outside air flow is controlled according to the temperature measured in the chamber atmosphere.

The device and the method are also applicable to the storage of apples under a controlled atmosphere. The atmosphere of the chamber is maintained with an oxygen level of the order of 2%. The $CO_2$ level is maintained between 2 and 5%, i.e. at a high value. The temperature is maintained at a low value, of the order of 0.5° C.

The flow rate of the atmosphere through the contacting device is adjusted according to the $CO_2$ concentration in the atmosphere of the chamber measured by the sensor 55. The liquid flow rate is adjusted according to the concentration of $CO_2$ and/or $O_2$ measured by the sensor 55 in the atmosphere of the chamber. The outside air flow rate in the external contacting device 95 is adjusted according to the temperature in the storage atmosphere.

It should be noted that, alternatively, the unit 1 according to the fourth embodiment of the invention may advantageously comprise, in place of the contacting device 31 of the type illustrated in FIG. 2, a subunit of the type illustrated in FIG. 4, with a device for bringing the atmosphere into contact with a water flow coming from the external device 95, and another device for bringing the liquid into contact with a biocidal and/or safener product.

It is important to note also that, in all embodiments, the system self-regulates. As the biocidal and/or safener product is vaporized at room temperature, lower than 50° C., it evaporates until saturation of the atmosphere without risk of supersaturation (which is the case when heating). This prevents the liquid from recondensing after injection. This is also true for the evaporation of water to humidify the atmosphere.

Thus, in addition to, or instead of, regulation by measuring the concentration of the product or the humidity in the atmosphere, it is intended to allow the system to self-regulate. For example, the system works continuously. The water or product at room temperature evaporates to saturation. Once the saturation is reached, there is no more evaporation.

What is claimed is:

1. A method for treating atmosphere of a storage of vegetable products having a volume greater than 200 m$^3$, wherein the method comprises:

providing a contacting device comprising a liquid reservoir containing a liquid, and packing placed above the liquid reservoir, wherein the liquid comprises at least one volatile safener product with a boiling temperature between 60 and 280° C., the at least one safener product being at least one selected from the group consisting of essential oil, terpenes, saturated or unsaturated C3 to C9 alcohol, isopropanol, iso-octanol, 2-ethylhexanol, glutaraldehyde, hexanal, dimethylnaphthalene and 3-decene-2-one, generating a liquid flow in which the liquid is supplied to an upper portion of the contacting device from the liquid reservoir, flows downward through the packing toward liquid reservoir, and collected in the liquid reservoir; and generating an atmosphere flow in which the atmosphere of the storage is introduced into the contacting device, flows upward through the packing, and is discharged from the contacting device into the storage, wherein the packing provides contact surfaces for the liquid and the atmosphere over which the atmosphere and the liquid contact with each other while the atmosphere flows upward through the packing and the liquid flow downward through the packing such that the liquid is evaporated at a temperature below 50° C. when contacting the atmosphere, and the atmosphere loaded with the evaporated liquid is discharged from the contacting device into the storage.

2. The method according to claim 1, wherein the method comprises:
   collecting the liquid flow resulting from contacting the atmosphere;
   regenerating the liquid flow resulting from contacting the atmosphere, during which the liquid flow is brought into contact with an air flow from outside the storage by circulation in an external packing, wherein the liquid flow is then reused in contacting the atmosphere.

3. The method according to claim 2, wherein the method comprises measuring a concentration of $CO_2$ and/or $O_2$ in the storage atmosphere, wherein a flow rate of the liquid flow is adjusted as a function of the measured concentration.

4. The method according to claim 2, wherein the method comprises measuring the temperature and/or humidity in the atmosphere of the storage, wherein a flow of the atmosphere when contacting the atmosphere with the liquid flow is adjusted as a function of the measured temperature and/or humidity.

5. The method according to claim 2, wherein the method comprises measuring the temperature in the storage atmosphere, wherein a flow rate of the outer air flow when regenerating the liquid flow is adjusted at least as a function of the measured temperature.

6. The method according to claim 1, wherein the contacting device comprises a packed tower comprising the packing.

7. The method according to claim 6, wherein the packed tower having a vertical axis.

8. The method according to claim 1, wherein the liquid reservoir containing the liquid is placed vertically under the packing.

9. The method according to claim 1, wherein the liquid flow is injected above the packing and collected in the liquid reservoir after flowing through the packing, the liquid being recycled from the liquid reservoir directly above the packing when contacting the atmosphere.

10. The method according to claim 1, wherein the packing comprises a structure offering the contact surfaces between the liquid flow and the atmosphere, the packing being made of a plastic material.

11. The method according to claim 1, wherein the packing is of a structured type.

12. The method according to claim 1, wherein the packing comprises a Raschig ring packing, a Pall ring packing or a honeycomb structured packing.

* * * * *